United States Patent
Umetsu

(10) Patent No.: US 7,884,942 B2
(45) Date of Patent: Feb. 8, 2011

(54) PROBE APPARATUS AND TERAHERTZ SPECTROMETER

(75) Inventor: Tomoyuki Umetsu, Tokyo (JP)

(73) Assignee: Sony Corporation, Tokyo (JP)

( * ) Notice: Subject to any disclaimer, the term of this patent is extended or adjusted under 35 U.S.C. 154(b) by 172 days.

(21) Appl. No.: 12/368,839

(22) Filed: Feb. 10, 2009

(65) Prior Publication Data
US 2009/0225311 A1 Sep. 10, 2009

(30) Foreign Application Priority Data
Mar. 4, 2008 (JP) .............................. 2008-053803

(51) Int. Cl.
*G01N 21/55* (2006.01)
(52) U.S. Cl. .................. 356/445; 250/336.1
(58) Field of Classification Search .............. 250/336.1; 356/445
See application file for complete search history.

(56) References Cited

U.S. PATENT DOCUMENTS

| | | | | |
|---|---|---|---|---|
| 5,789,750 A | * | 8/1998 | Nuss | 250/338.1 |
| 2003/0016358 A1 | * | 1/2003 | Nagashima et al. | 356/364 |
| 2004/0095147 A1 | * | 5/2004 | Cole | 324/629 |
| 2007/0158571 A1 | * | 7/2007 | Cole et al. | 250/341.8 |
| 2007/0242274 A1 | * | 10/2007 | Cluff | 356/445 |
| 2008/0179527 A1 | * | 7/2008 | Demers | 250/338.1 |
| 2008/0179528 A1 | * | 7/2008 | Demers | 250/338.1 |

FOREIGN PATENT DOCUMENTS

JP 2002-223017 8/2002

OTHER PUBLICATIONS

Inoue et al., "Development of fiber-coupled compact Terahertz time-domain spectroscopy imaging head", 2006, Japanese Journal of Applied Physics, vol. 45 No. 10A, pp. 7928-7932.*

* cited by examiner

*Primary Examiner*—Kara E Geisel
(74) *Attorney, Agent, or Firm*—K&L Gates LLP

(57) ABSTRACT

A probe apparatus includes a first focusing lens and a second focusing lens. The first focusing lens is arranged on a surface of a base to which a terahertz excitation beam is applied, the surface being opposite to the surface to which terahertz excitation beam is applied, with the lens axis deviated from the center of a point at which the terahertz excitation beam is applied. The second focusing lens is arranged on a surface of a base to which a terahertz detected beam is applied from a source of the terahertz excitation beam, the surface being opposite to the surface to which the terahertz detected beam is applied, with the lens axis deviated from the center of a point at which the terahertz detected beam is applied, in a direction opposite to the direction in which the lens axis of the first focusing lens is deviated.

9 Claims, 9 Drawing Sheets

PROBE APPARATUS AND TERAHERTZ SPECTROMETER

CROSS REFERENCES TO RELATED APPLICATIONS

The present application claims priority to Japanese Patent Application JP 2008-053803 filed in the Japanese Patent Office on Mar. 4, 2008, the entire contents of which is being incorporated herein by reference.

BACKGROUND

Hitherto known as a technique of generating or detecting terahertz waves is terahertz time-domain spectroscopy (TDS). As known in the art, the terahertz time-domain spectroscopy is suitable for use in imaging samples because it utilizes terahertz waves that define ultra-short pulses, as short as about 100 femtoseconds. Therefore, the terahertz time-domain spectroscopy attracts attention in various technical fields such as industry, medicine, biotechnology, agriculture and security.

In the terahertz time-domain spectroscopy, a pulse light beam emitted from an ultra-short laser source is split into a pump beam and a probe beam. The pump beam is focused on a terahertz-wave generating element. In the terahertz-wave generating element, a current flow is generated or electrical polarization develops for about subpico seconds, generating a terahertz wave having an electric-field amplitude proportional to the time derivative. The terahertz wave is focused by an optical system on a terahertz-wave detecting element. At this point, the probe beam is applied to the terahertz-wave detecting element. Then, the terahertz-wave detecting element generates a carrier. The carrier is accelerated by the electrical field of the terahertz wave and changed to an electric signal. The time at which the probe beam reaches the terahertz-wave detecting element is delayed, thereby measuring the time waveform the terahertz wave has in the amplification electric field. The time waveform is Fourier-transformed, thereby determining the spectrum of the terahertz wave.

The terahertz-wave generating element and the terahertz-wave detecting element can be identical in configuration. Such an element is described in, for example, Jpn. Pat. Appln. Laid-Open Publication No. 2002-223017. This publication discloses, in paragraph [0036], a terahertz beam element 21 that has a base 22, an optically conductive film 23 formed on the base 22, and electrically conductive films 24 and 25 formed on the optically conductive film 23. Note that a part of the base 22 functions as a lens.

The publication teaches, in paragraph [0040], that three or more electrically conductive films are formed on the optically conductive film 23, each, isolated from another at intervals d, thus forming an array of optical switch elements, and that the base 22 may form an array of lenses associated with the optical switch elements, respectively.

The terahertz time-domain spectroscopy is classified into so-called transmission type and so-called reflection type. In the transmission type, the terahertz-wave generating element and the terahertz-wave detecting element are arranged, facing each other across a sample. In the reflection type, the terahertz-wave generating element and the terahertz-wave detecting element are arranged, both facing a sample.

To use the terahertz beam element 21 disclosed in the publication, in the reflection-type terahertz time-domain spectroscopy, the base 22 may form a lens array. In this case, the terahertz wave applied from the terahertz beam element 21 used as a terahertz-wave generating element is reflected by the focusing plane of the sample and returns to the terahertz-wave generating element, without being applied to the terahertz beam element 21 used as terahertz-wave generating element. Consequently, the sample may not be measured.

An optical component such as a half mirror may be provided between the base 22 and the sample. In this case, the apparatus is larger than in the case where the optical component is not used, and a loss is made in the energy of the terahertz wave.

Two terahertz beam elements 21 may be used as a terahertz-wave generating element and a terahertz-wave detecting element, respectively, and arranged obliquely to the focusing plane of the sample. In this case, the terahertz beam elements 21 can hardly be arranged in the same plane.

Therefore desirable to propose a probe apparatus and a terahertz spectrometer that are simple in configuration and can yet measure samples.

SUMMARY

The present disclosure relates to a technique of using electromagnetic waves (terahertz wave) in a band of about $0.1 \times 10^{12}$ THz to $100 \times 10^{12}$ THz.

To achieve the above, a probe apparatus according to an embodiment includes: a first focusing lens arranged on a surface of a base to which a terahertz excitation beam is applied, the surface being opposite to the surface to which terahertz excitation beam is applied, with a lens axis deviated from the center of a point at which the terahertz excitation beam is applied; and a second focusing lens arranged on a surface of a base to which a terahertz detected beam is applied from a source of the terahertz excitation beam, the surface being opposite to the surface to which the terahertz detected beam is applied, with a lens axis deviated from the center of a point at which the terahertz detected beam is applied, in a direction opposite to the direction in which the lens axis of the first focusing lens is deviated.

A terahertz spectrometer according to an embodiment includes: a terahertz-wave generating element configured to be applied with a terahertz excitation beam; a first focusing lens arranged on a surface of a base to which a terahertz excitation beam is applied, the surface being opposite to the surface to which terahertz excitation beam is applied, with a lens axis deviated from the center of a point at which the terahertz excitation beam is applied; a terahertz-wave detecting element configured to be applied with a terahertz detected beam from a side where the terahertz excitation beam has been applied; a second focusing lens arranged on a surface of the base of the terahertz-wave detecting element, the surface being opposite to the surface to which the terahertz detected beam is applied, with a lens axis deviated from the center of a point at which the terahertz detected beam is applied, in a direction opposite to the direction in which the lens axis of the first focusing lens is deviated; and a measuring unit configured to measure a sample on the basis of a signal detected by the terahertz-wave detecting element.

The probe apparatus and the terahertz spectrometer according to an embodiment can be more compact than in the case where the first focusing lens and the second focusing lens are not arranged in the same plane. Further, since the lens axis of the first focusing lens is deviated from the center of a point at which the terahertz excitation beam is applied, the terahertz wave radiating from the point can be focused obliquely to that surface of the sample, on which the wave is focused. Since the lens axis of the second focusing lens is deviated from a point at which the terahertz detected beam is applied, in a direction opposite to the direction in which the lens axis of the first focusing lens is deviated, the terahertz wave reflected at that surface of the sample, on which the wave is focused can be focused at the point at which the terahertz detected beam is applied. Hence, the sample can be measured even if the first and second focusing lenses are arranged in the same plane. Thus, this application can provide a probe apparatus and a terahertz spectrometer that are simple in configuration and can yet measure samples.

Additional features and advantages are described herein, and will be apparent from the following Detailed Description and the figures.

DETAILED DESCRIPTION

An embodiment will be described with reference to the accompanying drawings.

(1) Overall Configuration of the Terahertz Spectrometer

Figure 1:
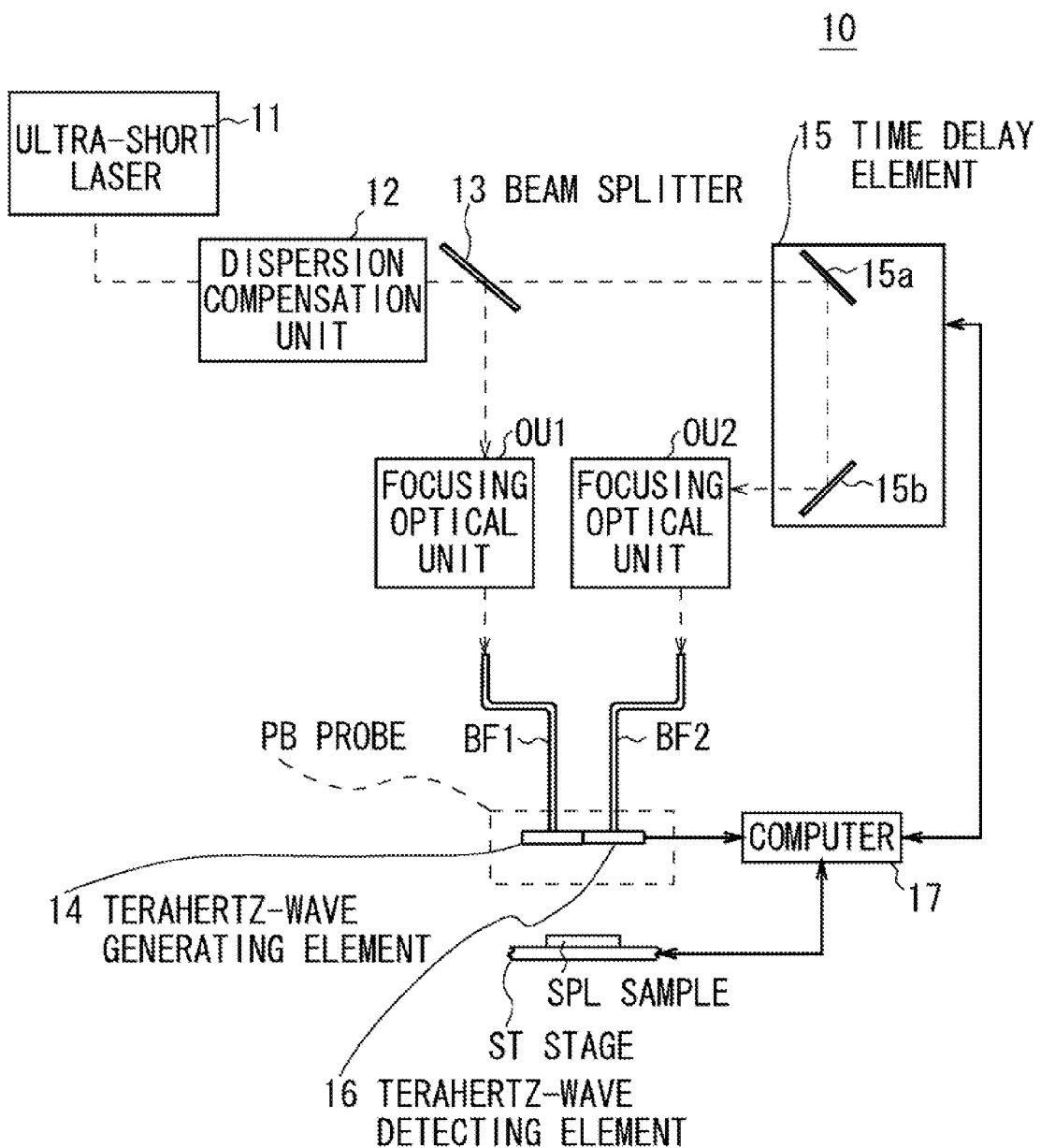
FIG. 1 is a schematic diagram showing the overall configuration of a terahertz spectrometer according to an embodiment.

FIG. 1 shows the overall configuration of a terahertz spectrometer 10 according to an embodiment. The terahertz spectrometer 10 includes an ultra-short laser 11, a dispersion compensation unit 12, a beam splitter 13, a terahertz-wave generating element 14, a time delay element 15, a terahertz-wave detecting element 16, and a computer 17.

The ultra-short laser 11 emits a pulse beam having, for example, a pulse width of about 100 fs, a pulse repetition frequency of about 80 MHz and a central wavelength of about 780 nm. This ultra-short laser beam light source LS is, in practice, a titanium laser or a sapphire laser, emitting femtosecond pulses.

The dispersion compensation unit 12 adjusts the pulse width of the pulse beam coming from the ultra-short laser 11, in a specific direction to achieve inverse correction of the pulse width diversion that has resulted from the wavelength-dependency of the refractive index of optical fibers BF1 and BF2.

The beam splitter 13 splits the pulse beam coming from the dispersion compensation unit 12 into an excitation pulse beam, which generates a terahertz wave, (hereinafter, also called "terahertz excitation beam") and a detected pulse beam, which detects a terahertz wave, (hereinafter called "terahertz detected beam").

The terahertz excitation pulse beam is guided by a focusing optical unit OU1 to the optical fiber BF1. The beam is then guided by a focusing lens (not shown) to the terahertz-wave generating element 14 provided in a probe PB. Meanwhile, the terahertz detected beam passes through the time delay element 15 is then guide by a focusing optical unit OU2 to the optical fiber BF2. After passing through the optical fiber BF2, the terahertz detected beam is focused by a focusing lens (not shown) on the terahertz-wave detecting element 16 provided in the probe PB.

The terahertz-wave generating element 14 generates a terahertz wave that has field amplitude proportional to the time derivative of the terahertz excitation beam. The terahertz-wave generating element 14 is, for example, a photoconductive antenna that includes a semiconductor substrate of Si, Ge, GaAs or the like, electrodes formed on the substrate and a voltage-applying unit for applying a bias voltage between the electrodes.

The time delay element 15 delays the time at which the terahertz detected beam reaches the terahertz-wave detecting element 16. In this embodiment, the time delay element 15 has a pair of mirrors 15a and 15b. One or both of the mirrors 15a and 15b are arranged movable. The optical path that extends between the mirrors 15a and 15b can therefore be changed to adjust the time at which the terahertz detected beam reaches the terahertz-wave detecting element 16.

The terahertz-wave detecting element 16 detects the terahertz wave generated in terahertz-wave generating element 14 and guided through a sample SPL (i.e., object used as reference measured object (control)). That is, the terahertz-wave detecting element 16 generates an electric field equivalent to the terahertz wave supplied to it from the sample SPL. When the terahertz-wave detecting element 16 receives the terahertz detected beam from the time delay element 15, it generates a signal that has a time waveform of the electric field equivalent to the terahertz wave. Like the terahertz-wave generating element 14, the terahertz-wave detecting element 16 is, for example, a photoconductive antenna.

The computer 17 is configured to acquire a signal (hereinafter called "first detection signal") input from the terahertz-wave detecting element 16 while the object remains, as sample SPL, on a mounting surface, and to acquire a signal (hereinafter called "second detection signal") input from the terahertz-wave detecting element 16 while the object remains, as the sample SPL or control, on the mounting surface. The second detection signal may be stored in the storage unit 44 beforehand and may be acquired from the storage unit provided in the computer 17, whenever necessary.

On acquiring the first detection signal and the second detection signal, the computer 17 extracts the amplitude data and phase data about the terahertz wave, from these detection signals. The computer 17 then acquires the information about the sample from the difference between the amplitude data and the phase data.

Thus, the computer 17 can achieve a higher S/N ratio than is possible with the Fourier spectroscopy that uses far-infrared beams and can acquire the amplitude data and the phase data at the same time. The computer 17 can therefore acquire information about the sample measured at high accuracy.

The computer 17 performs a control to move a stage ST in order to move the mirror 15a or the mirror 15b, or both, so that the optical path that extends between the mirrors 15a and 15b may have a prescribed length and that the mirrors 15a and 15b may be held at a prescribed height with respect to the sample SPL.

(2) Configuration of the Probe

Figure 2:
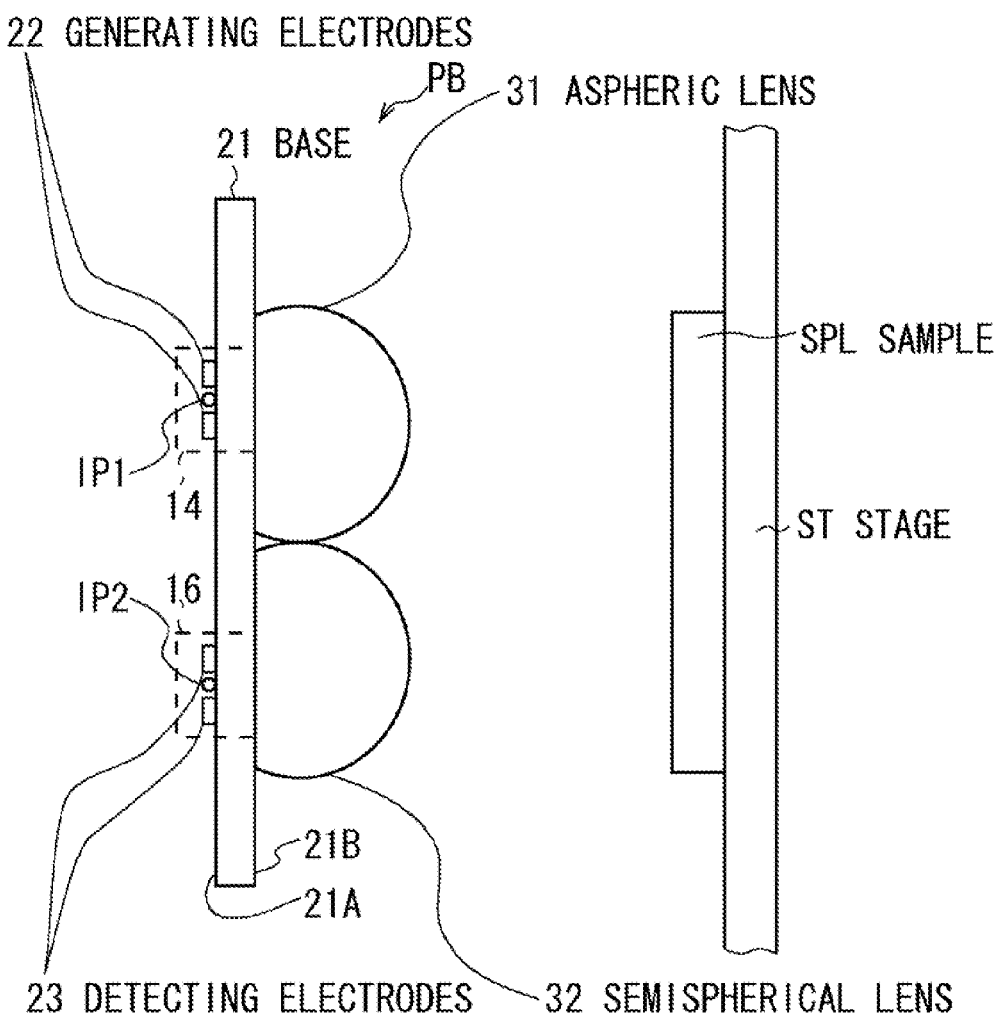
FIG. 2 is a schematic sectional view showing the configuration of a probe according to the embodiment.

The configuration of the probe PB will be described. As shown in FIG. 2, the probe PB has a base 21 made of Si, Ge, GaAs, or the like. The base 21 has a surface 21A that is scanned. Arranged on the surface 21A are electrodes 22 and 23. The electrodes 22 (hereinafter called "generating electrodes") are configured to generate a terahertz wave. The electrodes 23 (hereinafter called "detecting electrodes") are configured to detect a terahertz wave. The generating electrodes 22 and the detecting electrodes 23 are arranged at prescribed intervals. On the surface 21B of the base 21, which is opposite to the surface 21A, an aspheric lens 31 and a semispherical lens 32 are provided. The aspheric lens 31 is aligned with the generating electrodes 22, and the semispherical lens 32 is aligned with the detecting electrodes 23.

Figure 3:
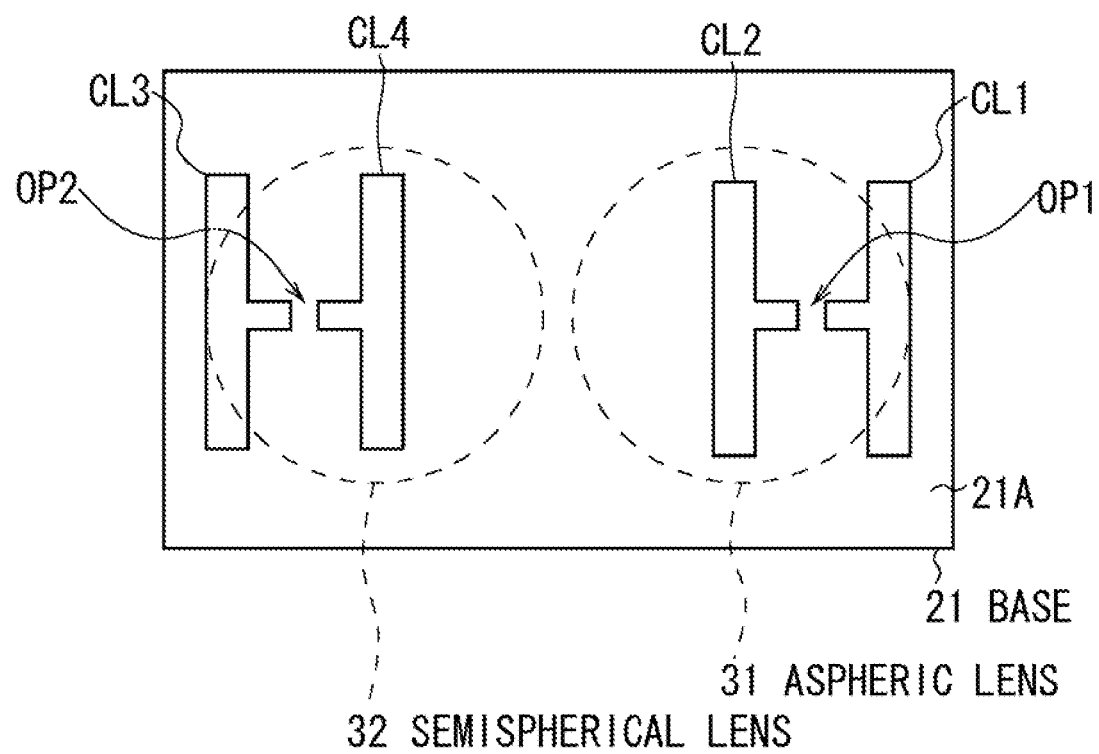
FIG. 3 is a schematic diagram showing the configurations of the electrodes incorporated in the probe.

As shown in FIG. 3, the generating electrodes 22 are a pair of parallel transmission lines CL1 and CL2. The middle parts of the parallel transmission lines CL1 and CL2 are close to each other, having a gap OP1 of several microns (μm) between them. Through this gap OP1, a terahertz excitation beam is applied from the optical fiber BF1 (FIG. 1).

Similarly, the detecting electrodes 23 have the same structure as the generating electrodes 22 and are a pair of parallel transmission lines CL3 and CL4. The parallel transmission lines CL3 and CL4 have a gap OP2 between them. Through this gap OP2, a terahertz detected beam is applied from the optical fiber BF2.

The aspheric lens 31 (FIG. 2) is made of silicon material, single crystal or polycrystalline. The lens 31 is shaped like a convex lens having a flat bottom and a curved top. The aspheric lens 31 focuses the terahertz wave radiating through the gap OP1 between the generating electrodes 22, in the focusing plane of a sample. Having only one aspheric lens 31, the probe PB can be smaller than, and can yet focus terahertz waves in the focusing plane with less aberration than, any probe that has a large-aperture mirror or a plurality of lenses.

In this terahertz spectrometer 10, the computer 17 adjusts, if necessary, the distance between from the focusing plane to the mounted surface of the sample SPL so that the focusing plane of the aspheric lens 31 and the reflection surface of the sample SPL may lie in flush with each other.

The semispherical lens 32 (FIG. 2) is made of silicon material, either single crystal or polycrystalline, and is shaped like a convex lens having a flat bottom and a curved top. The semispherical lens 32 focuses the terahertz wave reflected from the focusing plane, in the gap OP2 between the detecting electrodes 23. Having only one semispherical lens 32, the probe PB can be smaller than any probe that has a large-aperture mirror or a plurality of lenses, and can yet focus a terahertz wave on the terahertz-wave detecting element 16, more suppressing the reflection of the terahertz wave than any probe having a large-aperture mirror or a plurality of lenses.

Figure 4:
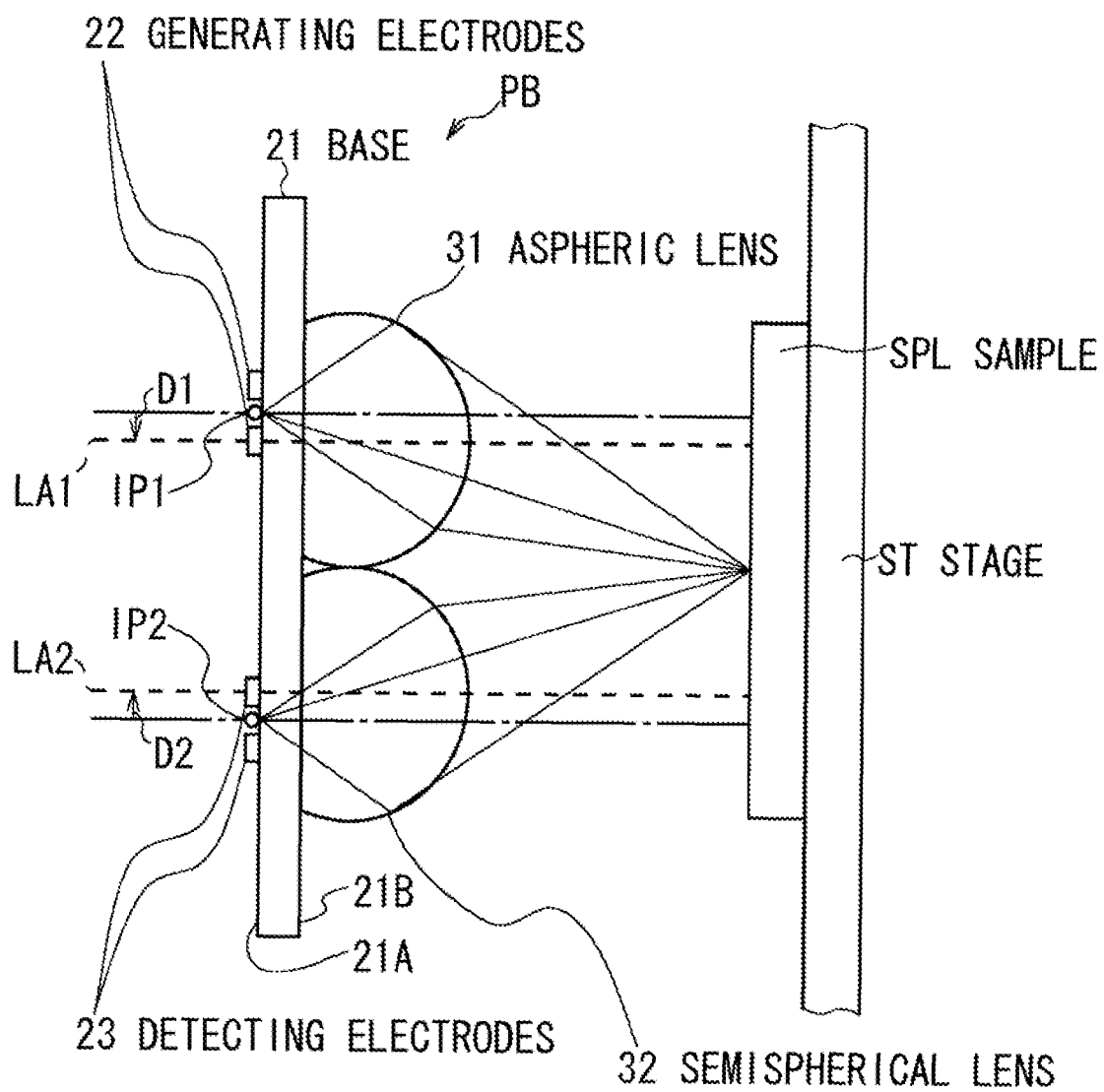
FIG. 4 is a schematic sectional view explaining the relationship between the lens and the points where an excitation beam and a detected beam are applied.

As shown in FIG. 4, the aspheric lens 31 is arranged, not having its axis LA1 (i.e., dashed line in FIG. 4) off the point IP1 at which the terahertz excitation beam is applied through the gap OP1 between the generating electrodes 22, but having its axis LA1 aligned with the point IP1, in the present embodiment.

Therefore, if the terahertz excitation beam is applied through the gap OP1 of the generating electrodes 22, the aspheric lens 31 will focus the terahertz wave radiating from the point IP1, in a direction oblique to the focusing plane (i.e., reflection surface of the sample SPL), as seen from the optical path shown in FIG. 4.

The semispherical lens 32 is arranged, not having its axis LA2 (i.e., dashed line in FIG. 4) off the point IP2 at which the terahertz detected beam is applied through the gap OP2 of the detecting electrodes 23, but having its axis LA2 aligned with the point IP2. That is, the axis LA2 deviates from the point IP2 in the direction D2 opposite to the direction D1 in which the axis LA1 of the aspheric lens 31 deviates from the point IP1.

Hence, as obvious from the optical paths shown in FIG. 4, the semispherical lens 32 focuses the terahertz wave reflected at the focusing plane of the sample SPL, in the gap OP2 between the detecting electrodes 23.

If the aspheric lens 31 and the semispherical lens 32 have the same aperture, the deviation of the lens axis LA1 from the point IP1 where the terahertz excitation beam is applied is equal to the deviation of the lens axis LA2 from the point IP2 where the terahertz detected beam is applied. If these deviations are different, the deviation of the lens axis LA1 or the deviation of the lens axis LA2 is increased or decreased, using the other deviation as reference.

(3) Operation and Effect

In the terahertz spectrometer 10 configured as described above, the aspheric lens 31 arranged on one surface 21B of the base 21 has its lens axis LA1 deviated from the point IP1 where the terahertz excitation beam is applied to the generating electrodes 22 arranged on the other surface 21A of the base 21.

On the other hand, the semispherical lens 32 arranged on the surface 21B of the base 21 has its lens axis LA2 deviated from the point IP2 where the terahertz detected beam is applied to the detecting electrodes 23 arranged on the other surface 21A of the base 21. More precisely, the axis LA2 deviates from the point IP2 in the direction D2 opposite to the direction D1 in which the axis LA1 of the aspheric lens 31 deviates from the point IP1 (see FIG. 2).

Thus, the terahertz spectrometer 10 can render the probe PB more compact than in the case where the generating electrodes 22, detecting electrodes 23, aspheric lens 31 and semispherical lens 32 are not arranged in the same plane. Although these components are arranged in the same plane, the terahertz wave radiated from the generating region of the generating electrodes 22 can be focused in a direction oblique to the focusing plane of the sample SPL. The terahertz wave reflected in the focusing plane of the sample SPL is thus focused in the detection region of the detecting electrodes 23. This sample SPL can therefore be measured.

In the terahertz spectrometer 10, a single base, i.e., base 21, holds both the terahertz-wave generating element 14 and the terahertz-wave detecting element 16 (see FIG. 2). Therefore, the terahertz spectrometer 10 can manufacture the probe PB more easily than in the case where two bases are used to hold the element 14 and the terahertz-wave detecting element 16. In addition, the measuring accuracy does not lower as in the case where bases holding the elements 14 and 16, respectively, move with respect to each other.

Further, the aspheric lens 31 (semispherical lens 32) is made of silicon material in the terahertz spectrometer 10. The aspheric lens 31 (semispherical lens 32) can therefore be adjusted to the base 21 in terms of refractive index. This can reduce the energy loss in the terahertz wave.

Moreover, the terahertz spectrometer 10 has one aspheric lens 31 (semispherical lens 32). Therefore, the number of lenses used and the sizes thereof are smaller than in the case where a spherical lens or a parabolic mirror is used. In addition, the aberration can be suppressed in the terahertz spectrometer 10.

Since the terahertz spectrometer 10 has one aspheric lens 31 (semispherical lens 32), the energy loss in the terahertz wave can be reduced. Further, no anti-reflection film is bonded to optical lenses for guiding terahertz waves in most cases to reduce the influence of multipath reflection, though anti-reflection film is bonded to the optical lenses for ordinary uses. In view of this, the use of a single lens is useful, particularly in the field of terahertz waves.

In the configuration described above, the aspheric lens 31 is arranged, having its axis LA1 off the center of the generating electrodes 22, where a terahertz wave is generated, and the semispherical lens 32 is arranged, having its axis LA2 off the center of the detecting electrodes 23, at which a terahertz wave is detected. Moreover, the axis LA2 of the semispherical lens 32 deviates from the center of the generating electrodes 22 in the direction D2 opposite to the direction D1 in which the axis LA1 of the aspheric lens 31 deviates from the center of the generating electrodes 22. The terahertz spectrometer 10 can therefore have a terahertz-wave generating system (emitter) and a terahertz-wave detecting system (detector) arranged in the same plane, and can generate and detect a terahertz wave. As a result, the embodiment can provide a terahertz spectrometer 10 that is compact and simple and can yet measure samples.

(4) Other Embodiments

The embodiment described above has a base 21 made of Si, Ge, GaAs, or the like. The present application is not limited to this. Instead, the base 21 may be one made of a nonlinear optical crystal such as ZnTe. If the base 21 is made of a nonlinear optical crystal, the generating electrode 22 and detecting electrode 23 need not be incorporated in the terahertz-wave generating element 14 and terahertz-wave detecting element 16.

In this case, the terahertz excitation beam and the terahertz detected beam are applied at a point in the surface 21A examined. The aspheric lens 31 and the semispherical lens 32 may be arranged on the surface 21B of the base 21, with their lens axes LA1 and LA2 deviated from the center of the surface 21A.

In the embodiment describe above, the aspheric lens 31 and the semispherical lens 32 have the same aperture (see FIG. 3 and FIG. 4). The present application is not limited to this, nevertheless. The aspheric lens 31 and the semispherical lens 32 may have different apertures. If they have different apertures, it suffices to increase or decrease the deviation of the lens axis LA1 or the deviation of the lens axis LA2, using the other deviation as reference. The same advantage can be attained as in the embodiment described above.

If a semispherical lens having a larger aperture than an aspheric lens is used, the beam condensing rate will increase. The sample SPL can then be measured even if the refection surface of the sample SPL has depressions and projections.

The embodiment described above has an aspheric lens 31. The present application is not limited to this, nevertheless. One or more refractive lenses may be used. As pointed out above, it is better to use one lens. Nonetheless, any lens that focuses terahertz waves can be used in whatever number and shape. This holds true of the semispherical lens 32, too.

In the embodiment described above, a pair of the generating electrode 22 and the detecting electrode 23, and the corresponding pair of the aspheric lens 31 and semispherical lens 32 are provided on the base 21. The embodiment is not limited to this configuration. A plurality of pairs of generating electrode and detecting electrode and the corresponding pairs of the aspheric lens and the semispherical lens may be arranged on the base 21.

Figure 5:
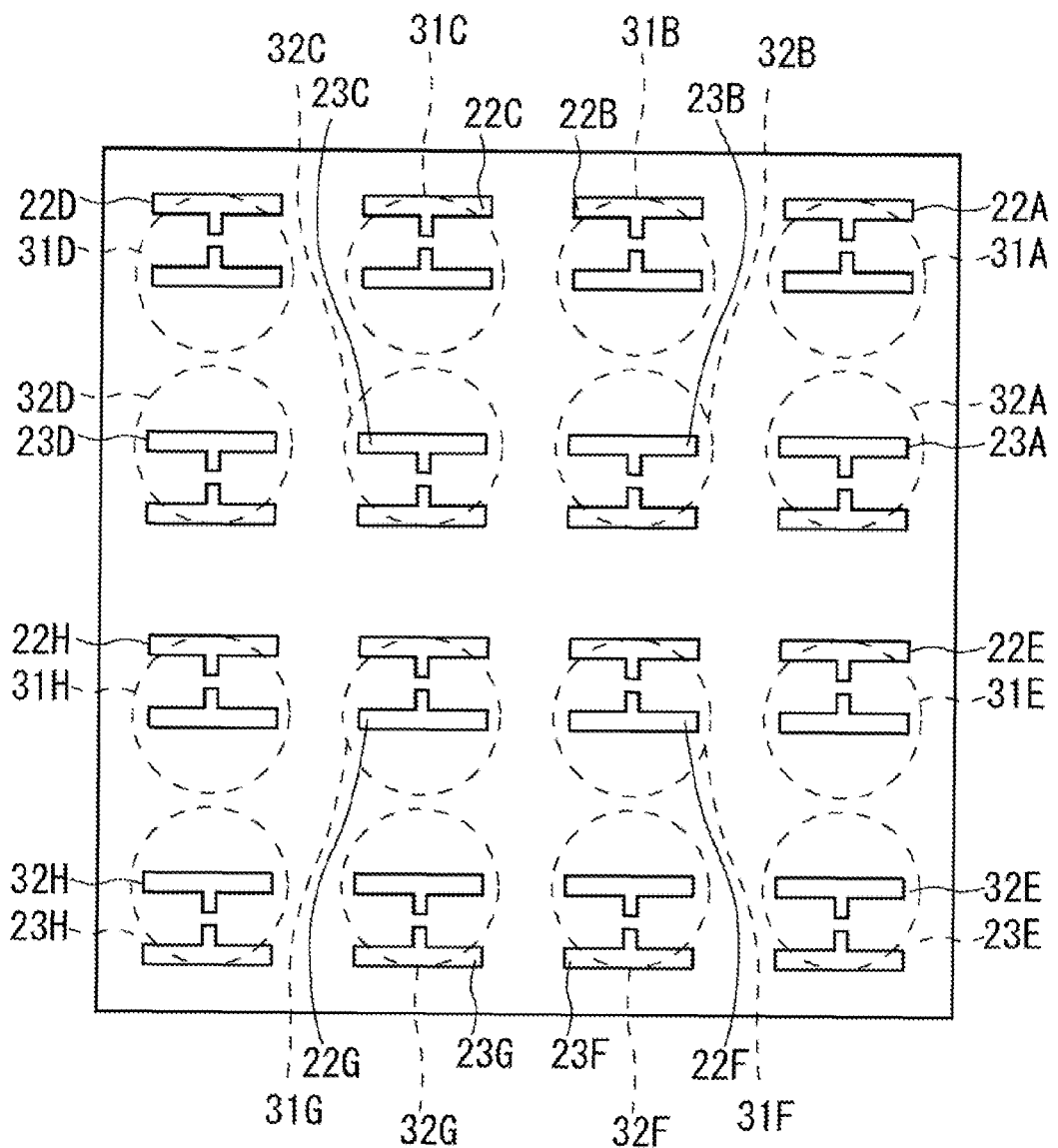
FIG. 5 is a schematic diagram showing the configuration (1-1) of a probe according to another embodiment.
Figure 6:
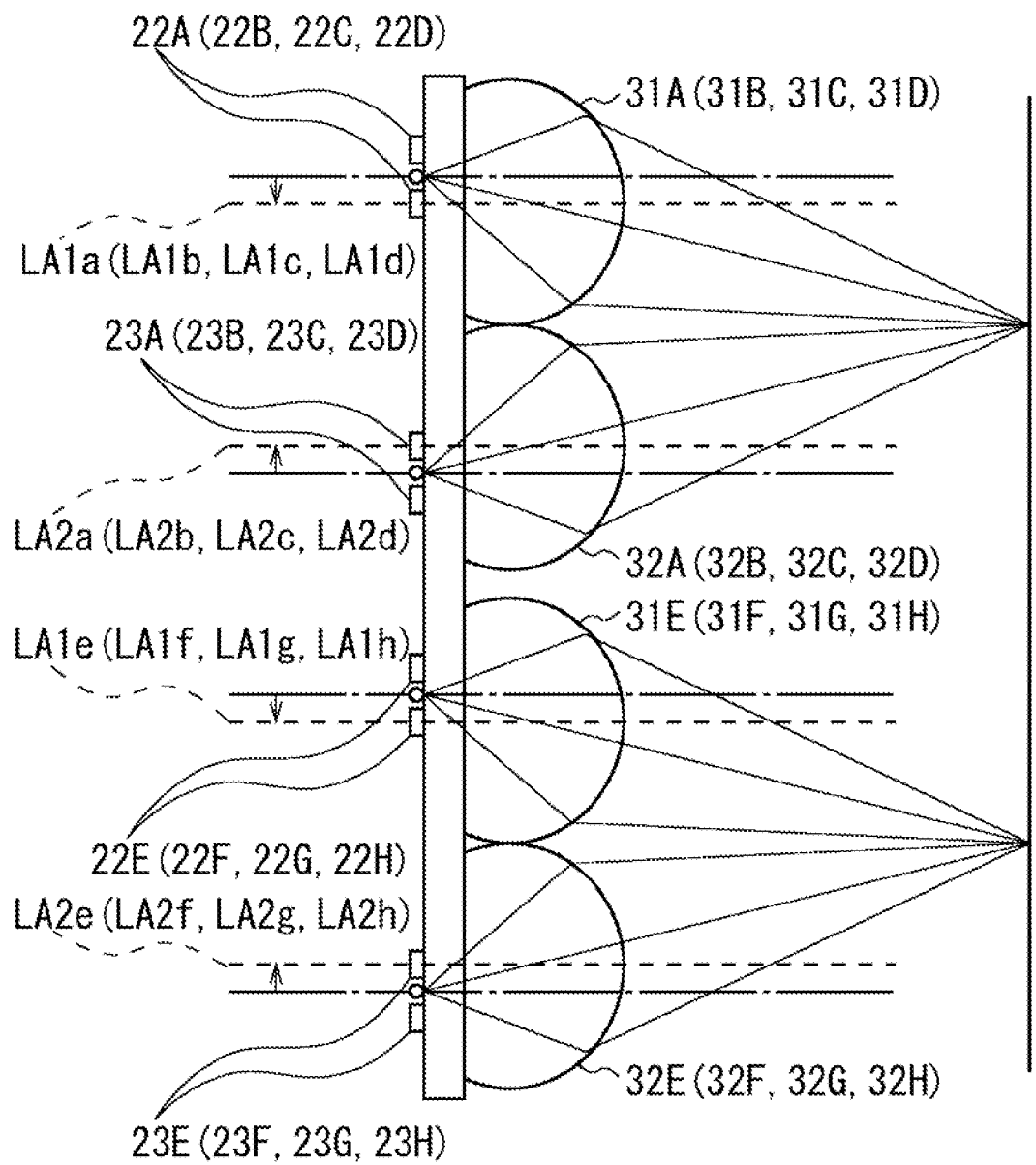
FIG. 6 is a schematic sectional view showing the configuration (1-2) of a probe according to a further embodiment.

A probe having pairs the generating electrode and the detecting electrode and the corresponding pairs of the aspheric lens and the semispherical lens is shown in FIGS. 5 and 6, in which the components identical to those shown in FIGS. 3 and 4 are designated by the same reference numbers. As shown in FIG. 5, on the base that a pair of the generating electrode 22 and the detecting electrode 23 adjacent each other constitutes an arrangement unit (pattern), eight pairs of the generating electrode and the detecting electrode (i.e. a generating electrode 22A and a detecting electrode 23A, . . . , a generating electrode 22H and a detecting electrode 23H) are arranged in two rows and four columns on the surface 21A examined of the probe. While, on the base that a pair of the aspheric lens 31 and the semispherical lens 32 adjacent each other constitutes an arrangement unit (pattern), eight pairs of the aspheric lens and the semispherical lens (i.e. an aspheric lens 31A and a semispherical lens 32A, . . . , an aspheric lens 31H and a semispherical lens 32H) are arranged in two rows and four columns on the surface 21B of the probe, which is opposite to the surface 21A examined.

As shown in FIG. 6, the aspheric lenses 31A to 31H are arranged on the surface 21B of the probe, which is opposite to the surface 21A examined, with their lens axes LA1a to LA1h deviated from the center of the point where the terahertz excitation beams are applied to the corresponding generating electrodes 22A to 22H. On the other hand, the semispherical lenses 32A to 32H are arranged on the surface 21B of the probe, which is opposite to the surface 21A examined, with their lens axes LA2a to LA2h deviated from the center of the point where the terahertz detected beams are applied to the corresponding detecting electrodes 23A to 23H. Note that the lens axes LA2a to LA2h are deviated in the direction D2 opposite to the direction D1 in which the axes LA1a to LA1h of the corresponding aspheric lenses 31A to 31H deviates and by the same distance as the axes LA1a to LA1h do.

This probe has a focusing optical unit OU1 that applies terahertz excitation beams to the generating electrodes 22A to 22H in the pairs. The focusing optical unit OU1 will be described with reference to FIG. 7.

Figure 7:
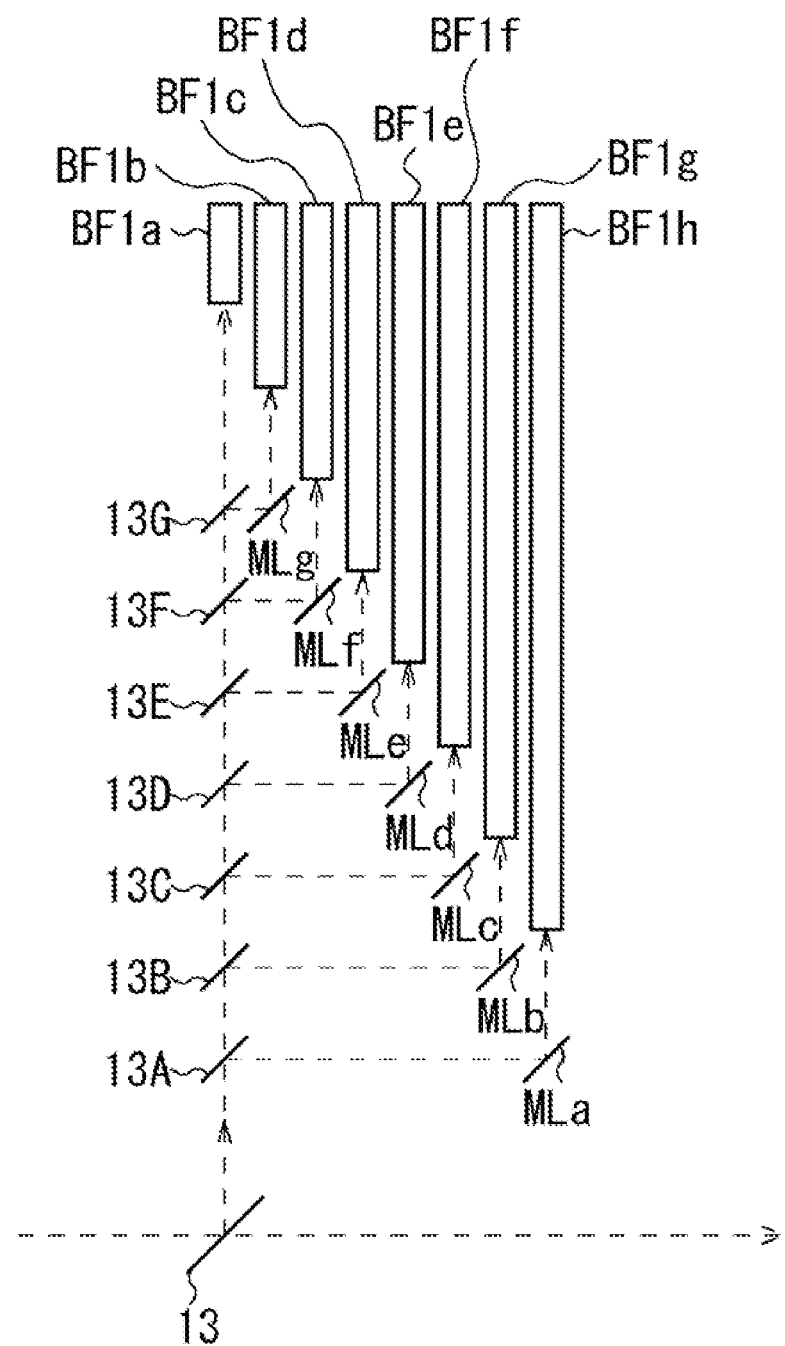
FIG. 7 is a schematic sectional view of a focusing optical system unit.

In the focusing optical unit OU1 shown in FIG. 7, seven beam splitters 13A to 13G splits the terahertz excitation beam coming from a beam splitter 13, into eight terahertz excitation beams. The eight terahertz excitation beams are applied to mirrors MLa to MLg, which reflect the eight terahertz excitation beams and guide them to optical fibers BF1h to BF1a, respectively. The optical fibers BF1a to BF1h can be bundled together, using the optical fiber BF1a as reference. The terahertz excitation beams pass through the optical fibers BF1a to BF1h. They are eventually applied to focusing lenses (not shown). The focusing lenses apply the terahertz excitation beams to the corresponding generating electrodes 22A to 22H. The probe has another focusing optical unit OU2, which is identical in configuration to the focusing optical unit OU1. The focusing optical unit OU2 can apply terahertz detected beams to the corresponding detecting electrodes 23A to 23H.

Pairs of the generating electrode and the detecting electrode are thus arranged. Therefore, a plurality of terahertz-wave generating systems (emitters) and a plurality of terahertz-wave detecting systems (detectors) can be arranged in the same plane, and a sample can be measured at many points.

Figure 8:
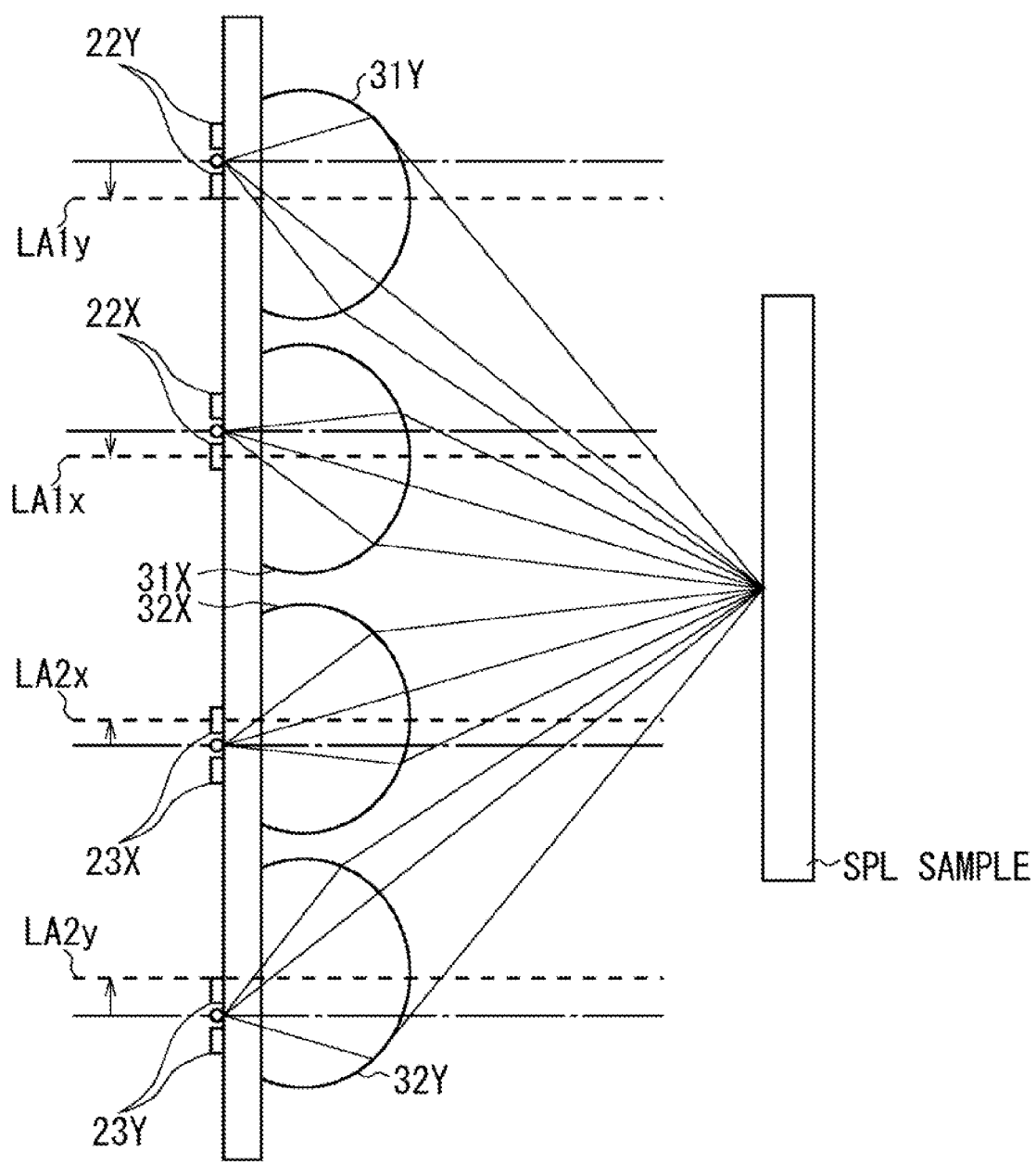
FIG. 8 is a schematic sectional view showing the configuration (2) of a probe according to still another embodiment.

In the probe of FIG. 6, each arrangement unit includes a pair of generating electrode and detecting electrode and a pair of an aspheric lens and a semispherical lens. Instead, any other arrangement units may be utilized. For example, as shown in FIG. 8, a pair of a generating electrode 22X and a detecting electrode 23X (an aspheric lens 31X and a semispherical lens 32X) adjacent each other and another pair of a generating electrode 22Y and a detecting electrode 23Y (an aspheric lens 31Y and a semispherical lens 32Y) that sandwich the pair of a generating electrode 22X and a detecting electrode 23X may constitute another arrangement unit. Arrangement units may be arranged in m rows and n columns (m and n are integers, one of which may be 0).

In the configuration of FIG. 8, the inner aspheric lens 31X and inner semispherical lens 32X have their lens axes LA1$x$ and LA2$x$ deviated less than the lens axe LA1$y$ and LA2$y$ of the outer aspheric lens 31Y and semispherical lens 32Y. Terahertz waves can therefore be focused at the same point.

The aspheric lenses 31X and 31Y may focus terahertz waves at the same position in the focusing plane (i.e., reflection surface of the sample SPL). Then, the terahertz waves can be intense (bright) at the focusing plane. As a result, the components that cooperate to generate terahertz waves can be more durable, than in the case where only one terahertz-wave generating element is used to intensify the terahertz wave.

Figure 9:
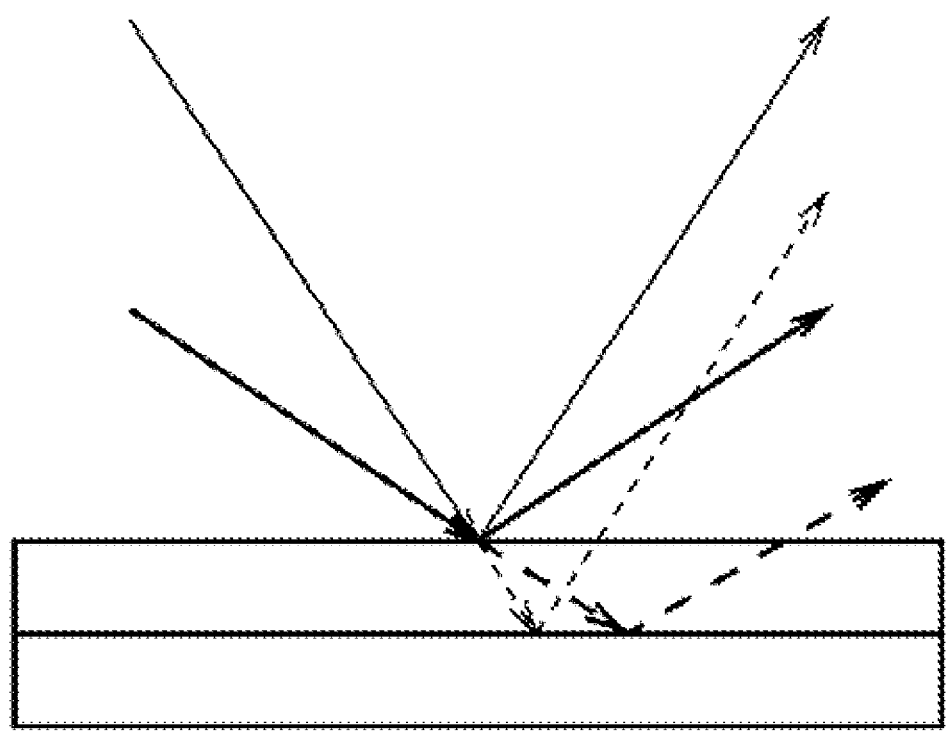
FIG. 9 is a schematic sectional view explaining how the depth to which the terahertz wave reaches depends on the incidence angle.

As shown in FIG. 9, terahertz waves are applied to the focusing plane (i.e., reflection surface of the sample SPL) at different incidence angles. The result of measuring therefore provides information about the depth to which the terahertz waves reach in the sample SPL (i.e., depth from the surface of the sample SPL). From the depth, information representing the transmittance of the sample SPL can be acquired. If a semispherical lens having a large aperture is used, beams applied at different incidence angles and reflected at different reflection angles will be detected.

Moreover, one detecting electrode (and one semispherical lens) and a plurality of generating electrodes (and aspheric lenses) may constitute an arrangement unit. Arrangement units of this configuration may then be arranged in m rows and n columns. In this case, the terahertz wave is more intense (more bright) at the focusing plane than in the probe of FIG. 6. This helps to acquire the information about the depth to which the terahertz waves reach in the sample SPL (i.e., depth from the surface of the sample SPL).

The base 21 may be demarcated into a plurality of areas, and different arrangement units may be provided in the respective areas, each arrangement unit including a pair of the generating electrode and the detecting electrode and the corresponding pair of the aspheric lens and the semispherical lens. Then, the sample SPL can be measured, area by area, in different ways.

Assume that pairs of the generating electrode and the detecting electrodes, and the corresponding pairs of the aspheric lens and semispherical lens are provided, and that a beam application unit is provided, which applies terahertz excitation beams to the points (i.e., gaps in the generating electrodes 22A to 22H in FIG. 6, or 22X and 22Y in FIG. 8) at which the terahertz excitation beam is applied and which is used as reference in the first focusing lens and is the one of the pair and applies terahertz detecting beams to the points (i.e., gaps in the detecting electrodes 23A to 23H in FIG. 6, or 23X and 23Y in FIG. 8) at which the terahertz detected beam is applied from second focusing lens, which is the other of the pair, at different timing according to the pairs, mixing of the terahertz waves can be avoided. The electrodes can therefore be arranged close to one another. This helps to render the probe still smaller.

The beam application unit may have a movable mirror, instead of the beam splitters 13A to 13G and mirrors MLa to MLg, all shown in FIG. 7. The movable mirror is inclined to different angles, guiding the terahertz excitation waves separated by the beam splitter 13 and the terahertz detected waves coming from the time delay element 15, one after another, to the pair of the generating electrode and the detecting electrode. The destination of the terahertz excitation beam and terahertz detected beam with respect to the optical fiber is thereby switched from one to another.

In the embodiment described above, the terahertz excitation beam and the terahertz detected beam are applied to a fixed point on the base 21. If the base 21 is replaced by one made of a nonlinear optical crystal, the application point of terahertz excitation beam or the application point of terahertz detected beam, or both application points may be switched.

To switch the application point, movable focusing lenses may be provided between the generating electrodes 22A to 22H (FIG. 6) and the optical fibers BF1$b$ to BF1$h$ (FIG. 7). Then the position of the movable lenses may be moved under the control of the computer 17 so that the position to be focused moves parallel to the focusing plane. Thereby, the application point can be switched. In this case, the advantage of the configuration shown in FIG. 8 can be attained, while employing the simple basic arrangement pattern shown in FIG. 6.

The configurations of the embodiments described above may be altered in any possible ways, as needed.

The embodiment can be utilized in various technical fields such as industry, medicine, biotechnology, agriculture, security, data communication and electronics.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A probe apparatus comprising:
   a first focusing lens arranged on a surface of a base to which a terahertz excitation beam is applied, the surface being opposite to a surface to which terahertz excitation beam is applied, with a lens axis deviated from the center of a point at which the terahertz excitation beam is applied; and
   a second focusing lens arranged on a surface of a base to which a terahertz detected beam is applied from a source of the terahertz excitation beam, the surface being opposite to a surface to which the terahertz detected beam is applied, with a lens axis deviated from the center of a point at which the terahertz detected beam is applied, in a direction opposite to the direction in which the lens axis of the first focusing lens is deviated.

2. The probe apparatus according to claim 1, wherein the base to which the terahertz excitation beam is applied and the base to which the terahertz detected beam is applied are a single base.

3. The probe apparatus according to claim 1, wherein the first focusing lens and the second focusing lens are aspheric lenses or spherical lenses.

4. The probe apparatus according to claim 3, wherein the aspheric lens or spherical lenses are made of single crystal silicon or polycrystalline silicon.

5. The probe apparatus according to claim 1, wherein the second focusing lens has a larger aperture than the first focusing lens.

6. The probe apparatus according to claim 1, comprising:

a plurality of pairs of terahertz-wave generating elements and terahertz-wave detecting elements; and a terahertz-wave applying unit configured to apply a terahertz excitation beam to the point at which the terahertz excitation beam is applied and which is used as reference in the first focusing lens of one of the pair and to apply a terahertz detected beam to the point at which the terahertz detected beam is applied and which is used as reference in the second focusing lens of the other of the pair, at different timing according to the pairs.

7. The probe apparatus according to claim 1, wherein a plurality of pairs of the first focusing lens and the second focusing lens are provided; and the deviation of the lens axes between the first focusing lens and the second focusing lens varies with the pairs.

8. The probe apparatus according to claim 1, wherein the first and the second focusing lenses adjacent each other and another first and second focusing lenses, which sandwich the first and the second focusing lenses adjacent each other, constitute an arrangement unit; and the lens axes of the first and second focusing lenses adjacent each other are less deviated than the lens axes of the other first and second focusing lenses, which sandwich the first and the second focusing lenses adjacent each other.

9. A terahertz spectrometer comprising:

a terahertz-wave generating element configured to be applied with a terahertz excitation beam;

a first focusing lens arranged on a surface of a base of the terahertz-wave generating element, the surface being opposite to a surface to which terahertz excitation beam is applied, with a lens axis deviated from the center of a point at which the terahertz excitation beam is applied;

a terahertz-wave detecting element configured to be applied with a terahertz detected beam from a side where the terahertz excitation beam has been applied;

a second focusing lens arranged on a surface of the base of the terahertz-wave detecting element, which is opposite to a surface to which the terahertz detected beam is applied, with a lens axis deviated from the center of a point at which the terahertz detected beam is applied, in a direction opposite to the direction in which the lens axis of the first focusing lens is deviated; and a measuring unit configured to measure a sample on the basis of a signal detected by the terahertz-wave detecting element.

* * * * *